United States Patent [19]

Yu et al.

[11] Patent Number: 5,686,489
[45] Date of Patent: *Nov. 11, 1997

[54] ALPHA HYDROXYACID ESTERS FOR SKIN AGING

[75] Inventors: Ruey J. Yu, Ambler; Eugene J. Van Scott, Abington, both of Pa.

[73] Assignee: Tristrata Technology, Inc., Wilmington, Del.

[*] Notice: The term of this patent shall not extend beyond the expiration date of Pat. No. 5,091,171.

[21] Appl. No.: 486,045

[22] Filed: Jun. 7, 1995

Related U.S. Application Data

[63] Continuation-in-part of Ser. No. 945,680, Dec. 23, 1986, abandoned.

[51] Int. Cl.$^6$ .............................. A61K 31/19; A61K 7/48
[52] U.S. Cl. .................. 514/557; 514/574; 514/844; 514/847; 514/873
[58] Field of Search ............................. 424/60; 514/844, 514/847, 873, 557, 574, 941

[56] References Cited

U.S. PATENT DOCUMENTS

| | | | |
|---|---|---|---|
| 1,772,975 | 8/1930 | Wieland | 514/557 |
| 2,118,566 | 5/1938 | De Wayne | 167/90 |
| 3,227,616 | 1/1966 | Van Wessem et al. | 167/91 |
| 3,666,863 | 5/1972 | Swanback | 424/316 |
| 3,689,668 | 9/1972 | Piette | 514/532 |
| 3,806,593 | 4/1974 | Swanback et al. | 424/28 |
| 3,879,537 | 4/1975 | Van Scott et al. | 424/311 |
| 3,920,835 | 11/1975 | Van Scott et al. | 514/557 |
| 3,984,566 | 10/1976 | Van Scott et al. | 424/283 |
| 3,988,470 | 10/1976 | Van Scott et al. | 424/283 |
| 3,991,184 | 11/1976 | Kludas et al. | 424/177 |
| 4,021,572 | 5/1977 | Van Scott et al. | 424/317 |
| 4,053,630 | 10/1977 | Yu et al. | 514/494 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,246,261 | 1/1981 | Van Scott et al. | 424/240 |
| 4,287,214 | 9/1981 | Van Scott et al. | 424/346 |
| 4,294,852 | 10/1981 | Wildnauer et al. | 424/317 |
| 4,363,815 | 12/1982 | Yu et al. | 424/274 |
| 4,380,549 | 4/1983 | Van Scott et al. | 424/317 |
| 4,507,319 | 3/1985 | Barratt et al. | 514/546 |
| 4,518,789 | 5/1985 | Yu et al. | 560/105 |
| 4,608,370 | 8/1986 | Aronsohn | 514/159 |
| 4,612,331 | 9/1986 | Barrett et al. | 514/558 |
| 4,834,076 | 5/1989 | Millet et al. | 128/65 |
| 4,929,722 | 5/1990 | Partain et al. | 536/20 |
| 4,983,382 | 1/1991 | Wilmott et al. | 424/62 |
| 5,021,450 | 6/1991 | McLane et al. | 514/460 |
| 5,091,171 | 2/1992 | Yu et al. | 514/349 |
| 5,093,109 | 3/1992 | Mausner | 424/63 |
| 5,108,751 | 4/1992 | Hagan et al. | 424/401 |
| 5,153,230 | 10/1992 | Jeffery | 514/847 |
| 5,360,824 | 11/1994 | Barker | 424/680 |
| 5,389,677 | 2/1995 | Yu et al. | 514/557 |

FOREIGN PATENT DOCUMENTS

| | | |
|---|---|---|
| 64399 | 7/1975 | Australia . |
| 007 785 | 2/1980 | European Pat. Off. . |
| 086 070 | 8/1983 | European Pat. Off. . |
| 273 202 | 7/1988 | European Pat. Off. . |
| 413 528 | 2/1991 | European Pat. Off. . |
| 413528 | 2/1991 | European Pat. Off. . |
| 2517413 | 11/1975 | Germany . |
| 3540175 | 5/1987 | Germany . |
| 752066 | 4/1975 | South Africa . |

OTHER PUBLICATIONS

Webster's Ninth New Collegiate Dictionary, Merriam–Webster Inc. (1985) p. 1272.
Chemical Abstracts 70:14330q (1967), Durafrourd.
Chemical Abstracts 85:25286r (1976), Hadhary, et al.
Chemical Abstracts 108:210190m (1988).
Dorland's Medical Dictionary, 26th Ed., Saunders, Philadelphia, PA (1981) 647, 696–97.
Neostrata Company Notice (1992).
Merck Index, 10th Ed., Rathway, New Jersey, (1983) p. 768.
Weiss, J.S., M.D., et al., "Topical Tretinoin in the Treatment of Aging Skin" *J. Amer. Acad. of Dermatology*, vol. 19 (1988) pp. 169–75.
Weiss, J.S., M.D., et al., "Topical Tretinoin Improves Photoaged Skin: A Double–blind Vehicle Controlled Study", *J. Amer. Medical Assn.*, vol. 259, No. 4 (1988) pp. 527–32.
Moisturizing and Emolliency Documentary, Unusual Moisturizers and Emollients: Patent Digest for 1966–1977, Cosmetics andToiletries, vol. 93, Apr. 1978, pp. 55–60.
Chemical Abstracts 65864w, Bleehen, S.S., Skin Bleaching Preparations, vol. 88 (1978).
Chemical Abstracts 79710x, Juhlin, L.A., Dermatologically Useful Composition, vol. 84 (1976).
Fredriksson, T. et al., Urea Creams in the Treatment of Dry Skin and Hand Dermatitis, Pharmacology and Therapeutics, pp. 442–44 (1975).
Blair, C., The Action of a Urea–Lactic Acid Ointment in Icthyosis, *British Journal of Dermatology* vol. 94 pp. 145–53 (1976).
Van Scott et al., Control of Keratinization with α–Hydroxyacids and Related Compounds, *Arch Dermatol* vol. 110 pp. 586–90 (1974).
Grice, K., et al.,Urea and Retinoic Acid in Ichthyosis and Their Effect on Transepidermal Water Loss and Water Holding Capacity of Stratum Corneum, *Acta Dermatovener* vol. 53 pp. 114–18 (1973).
Harry, R.G., The Principles and Practice of Modern Cosmetics, 6th Ed.,Chapters 6 and 39, (1973).

(List continued on next page.)

*Primary Examiner*—James J. Seidleck
*Assistant Examiner*—Michael A. Williamson
*Attorney, Agent, or Firm*—Foley and Lardner

[57] ABSTRACT

Alpha hydroxyacid esters and related compounds on topical application induced increased skin thickness due to new biosyntheses of dermal components including glycosaminoglycans, proteoglycans, collagen and elastin. Such dermal effects are desirable and beneficial for topical use and treatment of aging related integumental changes including age spots, skin lines, wrinkles, photoaging and aging skin.

42 Claims, No Drawings

OTHER PUBLICATIONS

Goldenberg, R.L., et al. Correlation of Skin Feel of Emollients to Their Chemical Structure, *J. Soc. Cosmet. Chem.*, vol. 22 pp. 635–54 (1971).

Sadik, F., O–T–C Products for Corns, Calluses, Warts, *Journal of the American Pharmaceutical Assocation*, vol. NS10, No. 1, pp. 8–12 (1970).

Osipow, L.I., Buffering Humectant for Cosmetics, *Drug and Cosmetic Industry*, vol. 88, No. 4, pp. 438–515 (1961).

Stern, E.C., Topical Application of Lactic Acid in the Treatment and Prevention of Certain Disorders of the Skin, *The Urologic and Cutaneous Review*, vol. 50, No. 2, pp. 106–7 (1946).

Darr, D., Topical Vitamin C Protects Skin from Ultraviolet Radiation–Induced Damage, *British Journal of Dermatology*, vol. 127 pp. 247–53 (1992).

Derwent Abstract 85–228562[37]for SU 1140785 (Feb.23, 1985), Gerchikov, et al.

Derwent Abstract 86–064922[10]for JP 61–015810 (Jan. 23, 1986), Nonogawa, Shuji YG.

Lavker, et al., "Changes in Skin Surface Patterns with Age," *Journal of Gerontology*, 35, No.2, pp. 348–354 (1980).

Aggarwal, R.R., et al., A Clinical Trial with Cotaryl Cream in Hyperkeratotic Skin Conditions, *Indian J. Dermatol. Venerbol.*, vol. 45, No. 6, pp.442–444 (1979).

Hunt et al., "Anaerobic Metabolism and Wound healing...", *The American Journal of Surgery*, 135: pp. 328–32 (1978).

Comstock, et al., "Effect of Lactate on Collagen Proline....," *Proceedings of the National Academy of Science*, 66: No.2, pp. 552–57 (1970).

Terry et al., "Implications of Heavy Chain Disease . . .," *Proceedings of the National Academy of Science*, 66: No.2, pp. 558–63 (1970).

Cimino et al., "Ability of Nonenzymic Nitration or . . .," *Proceedings of the National Academy of Science*, 66: No.2, pp. 564–71 (1970).

Chemical Abstracts No. 85:25286r, Chemical Abstracts, No. 4, p. 248, (1976).

ALPHA HYDROXYACID ESTERS FOR SKIN AGING

This application is a continuation-in-part of Ser. No. 06/945,680 filed Dec. 23, 1986 now abandoned.

FIELD OF THE INVENTION

This application relates to topical compositions employing alpha hydroxyacid esters and related compounds, which compositions effect beneficial changes in both the dermis and epidermis of the skin. This application also relates to methods of topical treatment of the skin to effect such beneficial changes, including increased syntheses or modulation of glycosaminoglycans, collagen and elastic fibers. Such dermal effects are desirable and beneficial for topical treatment of aging related skin changes.

DESCRIPTION OF THE PRIOR ART

In our U.S. Pat. No. 3,879,537 entitled "Treatment of Ichthyosiform Dermatoses" we described and claimed the use of topical compositions containing an alpha hydroxyacid to alleviate the symptoms of ichthyosis. In our U.S. Pat. No. 3,920,835 entitled "Treatment of Disturbed Keratinization" we described and claimed the use of topical compositions containing an alpha hydroxyacid to alleviate the symptoms of ache. In our U.S. Pat. No. 3,984,566 entitled "Method of Alleviating the Symptoms of Dandruff" we described and claimed the use of topical compositions containing an alpha hydroxyacid to improve the symptoms of dandruff.

In our U.S. Pat. No. 4,105,783 entitled "Therapeutic Treatment of Dry Skin"; U.S. Pat. No. 4,197,316 entitled "Treatment of Dry Skin"; and U.S. Pat. No. 4,380,549 entitled "Topical Treatment of Dry Skin", we described and claimed the use of topical compositions containing an alpha hydroxyacid to alleviate or improve the symptoms of dry skin. In our U.S. Pat. No. 4,234,599 entitled "Treatment of Skin Keratoses with Alpha Hydroxyacids and Related Compounds", we described and claimed the use of topical compositions containing an alpha hydroxyacid or the related compound to alleviate the symptoms of actinic or nonactinic skin keratoses. In our U.S. Pat. No. 4,363,815 entitled "Alpha Hydroxyacids, Alpha Ketoacids and Their Use in Treating Skin Conditions", we described and claimed the use of topical compositions containing certain alpha hydroxyacids or the related compounds to improve skin conditions characterized by inflammation or disturbed keratinization.

This application is a continuation-in-part of our application Ser. No. 06/945,680 filed Dec. 23, 1986, refiled Jan. 19, 1990, Ser. No. 07/469,738 entitled "Additives Enhancing Topical Actions of Therapeutic Agents", and is related to our application Ser. No. 07/393,749 filed Aug. 15, 1989 entitled "Amphoteric Compositions and Polymeric Forms of Alpha Hydroxyacids, and Their Therapeutic Use".

The parent application of Ser. No. 07/469,738 described in addition to the main subject certain compositions containing hydroxycarboxylic acids and the related ketocarboxylic acids for topical treatment of wrinkles and skin changes associated with aging. The related application of Ser. No. 07/393,749 described in addition to the main subject a topical treatment to alleviate or remedy warts, nail infections, age spots, wrinkles and aging related skin changes with a composition containing certain alpha hydroxyacids or the related compounds.

In our more recent U.S. patent application Ser. No. 07/683,437 filed Apr. 10, 1991, entitled "Compositions Comprising 2-Hydroxycarboxylic Acids and Related Compounds, and Methods for Alleviating Signs of Dermatologic Aging", we described and claimed compositions and the use of such compositions containing 2-hydroxycarboxylic acid or a related compound for use in alleviating or improving the dermatologic signs of aging, including changes or damage to skin, nail and hair associated with intrinsic aging, as well as changes or damage caused by extrinsic factors such as sunlight, radiation, air pollution, wind, cold, heat, dampness, chemicals, smoke and cigarette smoking.

In our most recent U.S. Pat. No. 5,385,938 entitled "Method of Using Glycolic Acid for Treating Wrinkles" and U.S. Pat. No. 5,389,677 entitled "Method of Treating Wrinkles Using Glycolic Acid", we described and claimed the use of compositions containing glycolic acid for topical treatment of skin wrinkles.

In the U.S. Pat. No. 3,806,593 entitled "Hygienic-Cosmetic Compositions", it was claimed that compositions containing ethyl lactate, isopropyl lactate and/or glycerol mono- or di-lactate and propylene glycol may be applied to the skin for preventing the formation of acne or decreasing already established acne.

In European Patent Application No. 88302058.8, dication salt of citric acid monoester having 10 to 18 carbon atoms in a topical composition has been disclosed as skin smoothing and softening agent. The dication salts are selected from alkali metals, ammonium, alkanol ammonium, etc.

In PCT International Patent Application No. PCT/EP93/02883, monoalkyl citrate having an alkyl group of 7 to 10 carbon atoms has been claimed as a solubilizing agent in perfumery, cosmetics, personal care and household products.

Albert M. Kligman described in U.S. Pat. No. 4,877,805 that photoaging or sun damaged skin includes loss of collagen fibers, abnormal changes in elastic fibers and deterioration of small blood vessels in the dermis of the skin. The dermal components which make up the fibers of the dermis become smaller and sparser with increasing age, usually in sundamaged facial skin. There is a great loss of collagen fibers resulting in looseness and easy stretchability of the skin; elastic fibers become abnormal so that the skin does not promptly snap back after being stretched.

In our prior disclosures we described that alpha hydroxyacids, alpha ketoacids and related compounds were therapeutically effective for various cosmetic and dermatologic conditions. We reported that alpha ketoacid esters also were therapeutically effective. However, alpha hydroxyacid esters were not reported to be therapeutically effective for skin conditions associated with disturbed keratinization.

SUMMARY OF THE INVENTION

We have now discovered that alpha hydroxyacid esters and related compounds on topical application cause substantial increase in skin thickness by stimulating new syntheses of glycosaminoglycans, proteoglycans, collagen and elastic fibers as shown by histologic studies. Such dermal actions are therapeutically beneficial for topical use of these compounds in management and treatment of aging related skin conditions including pigmented and non-pigmented age spots, skin lines, wrinkles, photodamage, photoaging and intrinsically aging skin.

Examples of the aforementioned compounds include ethyl glycolate, methyl lactate, diethyl tartrate and triethyl citrate. The related compounds include ethyl tropate, ethyl isocitrate, ethyl ascorbate, ethyl quinate and ethyl citramalate.

DETAILED DESCRIPTION OF THE INVENTION

A discussion of skin structure and cutaneous aging is helpful in the description of the instant invention on the dermal actions and effects produced by alpha hydroxyacid esters and related compounds. Human skin is comprised of two principal components, the outer epidermis and the underlying dermis, which is situated above the subcutaneous adipose or fat tissues.

The epidermis consists of four distinct layers: stratum corneum, stratum granulosum, stratum spinosum and stratum basale; in the skin of palms and soles only, there is normally one additional zone called the stratum lucidum between the stratum corneum and the stratum granulosum.

The stratum corneum or horny layer is comprised of numerous flattened dead cells called corneocytes. The granular layer, located below the stratum corneum, contains large granules of keratinous materials. The spinous layer or prickle cell layer is located below the granular layer and composed of keratinocytes. The basal cell layer, located below the spinous layer but above the dermis, is the only principal layer in the epidermis in which living cells normally replicate DNA and divide into daughter cells.

After a basal cell divides, one of the daughter cells migrates into the spinous layer where the cell starts to differentiate as a keratinocyte, wherein synthesis of keratin is initiated. As the keratinocyte continues to move outward and reaches the granular layer, more keratinous materials are synthesized as keratin filaments and large granules. The keratinocyte loses its nucleus in transit through the granular layer and thereupon dies to become a corneocyte without nucleus in the stratum corneum.

Normally, the granular layer is a few cell layers in thickness, and the stratum corneum may be 14–25 cell layers thick. Under normal conditions and in most skin areas, a keratinocyte takes 14 days to move outward from the basal cell layer to the granular layer, and a corneocyte takes 14 days to reach the outermost layer of the stratum corneum to be shed; the total time from basal cell layer to the surface is approximately 28 days. The entire sequence of epidermal terminal differentiation is called keratinization.

The dermis is comprised mainly of collagen, elastic fibers, glycosaminoglycans and proteoglycans including hyaluronic acid, dermatan sulfate and chondroitin sulfate formerly known as mucopolysaccharides. Fibroblasts, the predominant cells of the dermis, synthesize collagen, elastic fibers, proteoglycans and glycosaminoglycans. Collagen makes up approximately 77%, elastic fibers account for about 2%, and glycosaminoglycans constitute around 0.2% of the dry weight of the dermis. Collagen provides the tensile strength of and elastic fibers give resilience to the dermis. The glycosaminoglycans binds water to form a gelatinous mass between collagen and elastic fibers, which acts as a lubricant and shock absorber for the dermis during movement of the skin.

Cutaneous aging, while having epidermal concomitants, seems to involve primarily dermal and subcutaneous changes, and is caused by (a) internal factors alone, as in intrinsic aging and (b) external factors, as in extrinsic aging. Intrinsic aging is also known as natural or chronologic aging, and extrinsic aging is often called photoaging. "Photodamage" implies skin damage caused by chronic sun exposure. These terms may be described as follows.

Intrinsic aging of skin, in sun-protected skin of the upper arm and abdomen, is an inherent degenerative process due to declining physiologic functions and capacities. Such aging process may include qualitative and quantitative skin changes and includes diminished or defective synthesis of collagen and elastic fibers, and proteoglycans and glycosaminoglycans in the dermis. Signs of intrinsic aging include progressive thinning of skin, deepening of skin lines and fine wrinkles, lusterless skin surface, and loss of skin elasticity and recoilability. Although intrinsic aging of living creatures is neither reversible nor preventable, modification and improvement of skin signs associated with such aging process can be achieved through topical management.

Extrinsic aging of skin is a distinctive process caused by external factors which include sunlight, radiation, air pollution, wind, cold, dampness, heat, chemicals, smoke and cigarette smoking.

Photoaging of skin may be defined as destructive cutaneous changes caused by chronic exposure to sunlight. Signs of photoaging on the face and back of hands include coarse and deepened wrinkles due to changes and degeneration of collagen and elastic fibers; marked loss of elasticity and recoilability; leathery skin surface and skin lesions with abnormal pigmentation and increased numbers of age spots, pigmented spots, blotches and nodules. Histologically, the qualities and quantities of elastin and collagen tissues are changed. Normal elastin in tissues is replaced by abnormal elastin characterized as solar elastosis, and the normal collagen fibers are decreased.

Photodamage of skin, also called solar damage, may be defined as cutaneous damage caused by chronic exposure to solar radiation and is associated with development of neoplastic lesions. Skin disorders caused by photodamage include pre-malignant lesions, basal cell carcinomas, squamous cell carcinomas and malignant melanomas.

In accordance with the instant invention, the alpha hydroxyacid esters and related compounds may be classified into two groups, namely (I) alpha hydroxyacid esters and (II) miscellaneous hydroxyacid esters.

(I) Alpha Hydroxyacid Esters.

The first group is an ester of organic carboxylic acid in which one hydroxy group is attached to the alpha position carbon atom of the acid. The generic structure of such esters may be represented by the following Formula I:

$$(Ra)(Rb)C(OH)COORc \qquad (I)$$

wherein Ra and Rb independently are selected from the group consisting of H, F, Cl, I, Br, alkyl, aralkyl or aryl group of saturated or unsaturated, isomeric or non-isomeric, straight or branched chain or cyclic form, having 1 to 29 carbon atoms, and in addition Ra and Rb may carry OH, CHO, COOH and alkoxy group having 1 to 9 carbon atoms. Rc is alkyl, aralkyl or aryl group of saturated or unsaturated, isomeric or non-isomeric, straight or branched chain or cyclic form, having 1 to 19 carbon atoms. The esters may exist as stereoisomers as D, L, and DL forms when Ra and Rb are not identical. When a compound contains two or more carboxyl groups the ester can exist as partial or full ester form, such as monoethyl tartrate and diethyl tartrate; monoethyl citrate, diethyl citrate and triethyl citrate.

Thus, when Ra and Rb are alkyl, they independently can be within any of the groups of C1–C5, C6–C10, C11–C15, C16–C20, C21–C25 and C26–C29. When Rc is alkyl, it can be within any of the groups of C1–C5, C6–C10, C11–C15 and C16–C19. Compounds within the invention thus include all of the possible combinations of Ra, Rb and Rc. Included within the foregoing is a subgenus of compounds having Ra, Rb and Rc independently selected from C1–C12.

Typical alkyl, aralkyl and aryl groups for Ra, Rb and Rc include methyl, ethyl, propyl, isopropyl, butyl, pentyl, octyl, decyl, dodecyl, hexadecyl, benzyl, and phenyl, etc.

Alpha hydroxyacid esters of the first group may be further divided into (a) alkyl hydroxyacid esters, (b) aralkyl and aryl hydroxyacid esters, (c) polyhydroxyacid esters, (d) hydroxypolyacid esters and (e) polyhydroxypolyacid esters. The following are representative alpha hydroxyacid esters in each subgroup. While not every specie has been specifically recited by name, the present inventors specifically contemplate each and every such ester in which the alpha hydroxyacid ester contains a methyl, ethyl, propyl, isopropyl, butyl, pentyl, octyl, decyl, dodecyl, hexadecyl, benzyl and/or phenyl substitutent. Thus, for example, for the glycolic acid esters recited in compound (a)1 below, the inventors specifically envision and possess methods and compositions employing methyl glycolate, ethyl glycolate, propyl glycolate, isopropyl glycolate, butyl glycolate, pentyl glycolate, octyl glycolate, decyl glycolate, dodecyl glycolate, hexadecyl glycolate, benzyl glycolate and phenyl glycolate. Similarly, where two or more such substitutents are possible, such as with the hydroxypolyacid and polyhydroxypolyacid esters discussed below, the di- and tri-: methyl, ethyl, propyl, isopropyl, butyl, pentyl, octyl, decyl, dodecyl, hexadecyl, benzyl and/or phenyl substitutions are specifically contemplated.

(a) Alkyl hydroxyacid esters.

1. 2-Hydroxyethanoic acid esters (glycolic acid esters); methyl glycolate, ethyl glycolate, propyl glycolate, etc.
2. 2-Hydroxypropanoic acid esters (lactic acid esters); methyl lactate, ethyl lactate, propyl lactate, etc.
3. 2-Methyl 2-hydroxypropanoic acid esters (methyllactic acid esters); methyl methyllactate, ethyl methyllactate, propyl methyllactate, etc.
4. 2-Hydroxybutanoic acid esters; methyl alpha hydroxybutanoate, ethyl alpha hydroxybutanoate, propyl alpha hydroxybutanoate, etc.
5. 2-Hydroxypentanoic acid esters; methyl alpha hydroxypentanoate, ethyl alpha hydroxypentanoate, propyl alpha hydroxypentanoate, etc.
6. 2-Hydroxyhexanoic acid esters; methyl alpha hydroxyhexanoate, ethyl alpha hydroxyhexanoate, propyl alpha hydroxyhexanoate, etc.
7. 2-Hydroxyheptanoic acid esters; methyl alpha hydroxyheptanoate, ethyl alpha hydroxyheptanoate, propyl alpha hydroxyheptanoate, etc.
8. 2-Hydroxyoctanoic acid esters; methyl alpha hydroxyoctanoate, ethyl alpha hydroxyoctanoate, propyl alpha hydroxyoctanoate, etc.
9. 2-Hydroxynonanoic acid esters; methyl alpha hydroxynonanoate, ethyl alpha hydroxynonanoate, propyl alpha hydroxynonanoate, etc.
10. 2-Hydroxydecanoic acid esters; methyl alpha hydroxydecanoate, ethyl alpha hydroxydecanoate, propyl alpha hydroxydecanoate, etc.
11. 2-Hydroxyundecanoic acid esters; methyl alpha hydroxyundecanoate, ethyl alpha hydroxyundecanoate, propyl alpha hydroxyundecanoate, etc.
12. 2-Hydroxydodecanoic acid esters (alpha hydroxylauric acid esters); methyl alpha hydroxylaurate, ethyl alpha hydroxylaurate, propyl alpha hydroxylaurate, etc.
13. 2-Hydroxytetradecanoic acid esters (alpha hydroxymyristic acid esters); methyl alpha hydroxymyristate, ethyl alpha hydroxymyristate, propyl alpha hydroxymyristate, etc.
14. 2-Hydroxyhexadecanoic acid esters (alpha hydroxypalmitic acid esters); methyl alpha hydroxypalmitate, ethyl alpha hydroxypalmitate, propyl alpha hydroxypalmitate, etc.
15. 2-Hydroxyoctadecanoic acid esters (alpha hydroxystearic acid esters); methyl alpha hydroxystearate, ethyl alpha hydroxystearate, propyl alpha hydroxystearate, etc.
16. 2-Hydroxyeicosanoic acid esters (alpha hydroxyarachidonic acid esters); methyl alpha hydroxyarachidonate, ethyl alpha hydroxyarachidonate, propyl alpha hydroxyarachidonate, etc.
17. 2-Hydroxytetraeicosanoic acid esters (cerebronic acid esters); methyl cerebronate, ethyl cerebronate, propyl cerebronate, etc.
18. 2-Hydroxytetraeicosenoic acid esters (alpha hydroxynervonic acid esters); methyl alpha hydroxynervonate, ethyl alpha hydroxynervonate, propyl alpha hydroxynervonate, etc.

(b) Aralkyl and aryl 2-hydroxycarboxylic acid esters.

1. 2-Phenyl 2-hydroxyethanoic acid esters (mandelic acid esters); methyl mandelate, ethyl mandelate, propyl mandelate, etc.
2. 2,2-Diphenyl 2-hydroxyethanoic acid esters (benzilic acid esters); methyl benzilate, ethyl benzilate, propyl benzilate, etc.
3. 3-Phenyl 2-hydroxypropanoic acid esters (phenyllactic acid esters); methyl phenyllactate, ethyl phenyllactate, propyl phenyllactate, etc.
4. 2-Phenyl 2-methyl 2-hydroxyethanoic acid esters (atrolactic acid esters); methyl atrolactate, ethyl atrolactate, propyl atrolactate, etc.

(c) Polyhydroxyacid esters.

1. 2,3-Dihydroxypropanoic acid esters (glyceric acid esters); methyl glycerate, ethyl glycerate, propyl glycerate, benzyl glycerate, phenyl glycerate, etc.
2. 2,3,4-Trihydroxybutanoic acid esters (isomers; erythronic acid esters, threonic acid esters); methyl erythronate, ethyl erythronate, methyl threonate, ethyl threonate, etc.
3. 2,3,4,5-Tetrahydroxypentanoic acid esters (isomers; ribonic acid esters, arabinoic acid esters, xylonic acid esters, lyxonic acid esters); methyl ribonate, ethyl ribonate, methyl arabinoate, ethyl arabinoate, methyl xylonate, ethyl xylonate, methyl lyxonate, ethyl lyxonate, etc.
4. 2,3,4,5,6-Pentahydroxyhexanoic acid esters (isomers; allonic acid esters, altronic acid esters, gluconic acid esters, mannoic acid esters, gulonic acid esters, idonic acid esters, galactonic acid esters, talonic acid esters); methyl allonate, ethyl allonate, methyl altronate, ethyl altronate, methyl gluconate, ethyl gluconate, methyl mannoate, ethyl mannoate, methyl gulonate, ethyl gulonate, methyl idonate, ethyl idonate, methyl galactonate, ethyl galactonate, methyl talonate, ethyl talonate, etc.
5. 2,3,4,5,6,7-Hexahydroxyheptanoic acid esters (isomers; glucoheptonic acid esters, galactoheptonic acid esters, etc.); methyl glucoheptonate, ethyl glucoheptonate, methyl galactoheptonate, ethyl galactoheptonate, etc.
6. Glyceruronic acid esters; methyl glyceruronate, ethyl glyceruronate, propyl glyceruronate, etc.
7. Erythruronic acid esters; methyl erythruronate, ethyl erythruronate, propyl erythruronate, etc.

8. Threuronic acid esters; methyl threuronate, ethyl threuronate, propyl threuronate, etc.
9. Riburonic acid esters; methyl riburonate, ethyl riburonate, propyl riburonate, etc.
10. Arabinuronic acid esters; methyl arabinuronate, ethyl arabinuronate, propyl arabinuronate, etc.
11. Xyluronic acid esters; ethyl xyluronate, ethyl xyluronate, propyl xyluronate, etc.
12. Lyxuronic acid esters; methyl lyxuronate, ethyl lyxuronate, propyl lyxuronate, etc.
13. Alluronic acid esters; methyl alluronate, ethyl alluronate, propyl alluronate, etc.
14. Altruronic acid esters; methyl altruronate, ethyl altruronate, propyl altruronate, etc.
15. Glucuronic acid esters; methyl glucuronate, ethyl glucuronate, propyl glucuronate, etc.
16. Mannuronic acid esters; methyl mannurate, ethyl mannurate, propyl mannurate, etc.
17. Guluronic acid esters; methyl guluronate, ethyl guluronate, propyl guluronate, etc.
18. Iduronic acid esters; methyl iduronate, ethyl iduronate, propyl iduronate, etc.
19. Galacturonic acid esters; methyl galacturonate, ethyl galacturonate, propyl galacturonate, etc.
20. Taluronic acid esters; methyl taluronate, ethyl taluronate, propyl taluronate, etc.

(d) Hydroxypolyacid esters.
1. 2-Hydroxypropane-1,3-dioic acid esters (tartronic acid esters); methyl tartronate, ethyl tartronate, propyl tartronate, etc.
2. 2-Hydroxybutane-1,4-dioic acid esters (malic acid esters); monomethyl malate, dimethyl malate, monoethyl malate, diethyl malate, monopropyl malate, dipropyl malate, etc.
3. 2,3-Dihydroxybutane-1,4-dioic acid esters (tartaric acid esters); monomethyl tartarate, dimethyl tartarate, monoethyl tartarate, diethyl tartarate, monopropyl tartarate, dipropyl tartarate, etc.
4. 3-Hydroxy-3-carboxypentane-1,5-dioic acid esters (citric acid esters); monomethyl citrate, dimethyl citrate, trimethyl citrate, monoethyl citrate, diethyl citrate, triethyl citrate, monopropyl citrate, dipropyl citrate, tripropyl citrate, etc.

(e) Polyhydroxypolyacid esters.
1. 2,3,4,5-Tetrahydroxyhexane-1,6-dioic acid esters (isomers; saccharic acid or glucaric acid esters, mucic acid or galactaric acid esters, etc.); monomethyl glucarate, dimethyl glucarate, monoethyl glucarate, diethyl glucarate, monopropyl glucarate, dipropyl glucarate, monoethyl galactarate, dimethyl galactarate, monoethyl galactarate, diethyl galactarate, monopropyl galactarate, dipropyl galactarate, dipropyl galactarate, etc.

(II) Miscellaneous Hydroxyacid Esters.
This group is an organic carboxylic acid ester in which one hydroxyl group is attached to the carbon atom other than at alpha position of the acid, for example beta hydroxyacid esters. It also includes substituted hydroxyacids, miscellaneous hydroxyacid esters and alpha ketoacid esters which are not readily represented by the foregoing generic structure. This group of compounds includes the following.
1. 3-Hydroxybutanoic acid esters (β-hydroxybutanoic acid esters); methyl 3-hydroxybutanoate, ethyl 3-hydroxybutanoate, propyl 3-hydroxybutanoate, etc.
2. Ascorbic acid and isoascorbic acid esters; methyl ascorbate, ethyl ascorbate, propyl ascorbate, etc.
3. Quinic acid esters; methyl quinate, ethyl quinate, propyl quinate, etc.
4. Isocitric acid esters; isocitric acid monomethyl ester, isocitric acid dimethyl ester, isocitric acid trimethyl ester; isocitric acid monoethyl ester, isocitric acid diethyl ester, isocitric acid triethyl ester; isocitric acid monopropyl ester, isocitric acid dipropyl ester, isocitric acid tripropyl ester, etc.
5. Tropic acid esters; methyl tropate, ethyl tropate, propyl tropate, etc.
6. Trethocanic acid esters; methyl trethocanate, ethyl trethocanate, propyl trethocanate, etc.
7. 3-Chlorolactic acid esters; methyl 3-chlorolactate, ethyl 3-chlorolactate, propyl 3-chlorolactate, etc.
8. Citramalic acid esters; citramalic acid monomethyl ester, citramalic acid dimethyl ester, citramalic acid trimethyl ester; citramalic acid monoethyl ester, citramalic acid diethyl ester, citramalic acid triethyl ester; citramalic acid monopropyl ester, citramalic acid dipropyl ester, citramalic acid tripropyl ester, etc.
9. Agaricic acid esters; methyl agaricate, ethyl agaricate, propyl agaricate, etc.
10. Aleuritic acid esters; methyl aleuritate, ethyl aleuritate, propyl aleuritate, etc.
11. Pantoic acid esters; methyl pantoate, ethyl pantoate, propyl pantoate, etc.
12. Lactobionic acid esters; methyl lactobionate, ethyl lactobionate, propyl lactobionate, etc.
13. Piscidic acid esters (p-hydroxybenzyltartaric acid esters); monomethyl piscidate, dimethyl piscidate, monoethyl piscidate, diethyl piscidate, monopropyl piscidate, dipropyl piscidate, etc.
14. Hexulosonic acid esters (2-keto-3,4,5,6-tetrahydroxyhexanoic acid esters); methyl hexulosonate, ethyl hexulosonate, propyl hexulosonate, etc.

In addition to the above alpha hydroxyacid esters and related compounds, free alpha hydroxyacids can also induce increased skin thickness due to biosynthesis of glycosaminoglycans, proteoglycans, collagen and elastin. These free alpha hydroxyacids include all the parent hydroxyacids, piscidic acid (p-hydroxybenzyltartaric acid), lactobionic acid, ascorbic acid, isoascorbic acid, quinic acid, isocitric acid, tropic acid and citramalic acid.

Certain esters of the instant invention may form a lactone. These esters include partially esterified alpha hydroxyacids having two or more carboxyl groups, for example monoethyl citrate lactone, monoethyl isocitrate lactone, monoethyl glucarate lactone, monoethyl galactarate lactone, etc.

Compositions containing the esters of the instant invention may be applied directly to the skin for treatment of aging related skin changes including pigmented and non-pigmented age spots, skin lines, wrinkles and photoaging without any external activation or stimulation of the skin. By positively affecting changes in the dermis, visible changes in the skin will occur. For example, wrinkles and skin lines will be visibly reduced or eradicated, the skin will appear plumper and more full, and the skin thus will attain a younger or more youthful appearance.

We have also found that the compositions of the instant invention can be applied to the skin after skin activation or stimulation by external factors, for example photostimulation by sunlight, skin activation from physiologic or pathologic stimulation or chemical substance.

Compositions containing alpha hydroxyacid esters or related compounds may incorporate a chemical substance that acts as a skin activator. Such activator may be a alpha hydroxyacid, alpha ketoesters, or any other compound which can provoke skin stimulation. The alpha hydroxyacids, alpha ketoacids and related compounds discussed below, can be in the form of a free acid or a salt or a reaction product with an amphoteric or pseudoamphoteric agent. Such activators include glycolic acid, lactic acid, citric acid, methyllactic acid, pyruvic acid, ethyl pyruvate, and many other alpha hydroxyacids as discussed more fully below, retinaldehydes, retinoic acid ("retin-A"), nicotinic acid. In general, the amount of skin activator used is less than that of the esters used in the composition. When alpha hydroxyacids, alpha ketoacids, and related compounds are employed, the concentration will range from at least about one or two percent to as much as five or ten percent or higher.

The compositions of the instant invention may contain one or more esters to magnify the therapeutic effect of unrelated topical agents which are present in the composition. It is believed that such incorporation results in magnified therapeutic efficacies which are not due to simple additive effects. The topical agents which may be incorporated into the composition include: agents (other than the esters of the present invention) that improve or eradicate pigmented or non-pigmented age spots, keratoses and wrinkles; antimicrobial and antiacne agents; antipruritic and antixerotic agents; antiinflammatory agents; sunscreen and antiphotosensitive agents; wart removers; skin lightening agents; depigmenting agents; local anesthetics and analgesics; corticosteroids; retinoids; vitamins; hormones; and antimetabolites.

Some examples of topical agents include acyclovir, amphotericins, chlorhexidine, clotrimazole, ketoconazole, econazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, salicylic acid, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate).

General Preparation of Compositions

In most cases compositions of the instant invention may be formulated as solution, gel, lotion, cream, ointment, balm, spray or other topically acceptable form, although in some instances, the esters of this invention may be used directly without formulation. To prepare a composition in solution form for general use, at least one ester is dissolved in a solution prepared from ethanol, water, propylene glycol, butylene glycol or other topically acceptable vehicle.

The concentration of the ester used may range from a minimum of about 1% or 2% to a maximum of 100%, the preferred concentration ranges being at least from 3%, 4% or 5% at minimum. As exemplified below, concentrations in the ranges of 40%, 50%, 60%, or more routinely can be employed. Indeed, esters such as ethyl glycolate and triethyl citrate which are in liquid form at room temperature may be applied topically to the skin in 100% concentration. Thus, typical ranges will be from about 1%, 2%, 3%, 4% or 5% at the minimum to 100% at maximum, and within that range will be ranges of from about 5% to about 10%, from about 10% to about 20%, from about 20% to about 40%, from about 40% to about 60%, from about 60% to about 80%, from about 80% to about 100%.

In the preparation of a composition in lotion, cream, ointment, balm or spray form, at least one ester is initially dissolved in a solvent such as ethanol, butylene glycol, propylene glycol or nonoxynol. The solution thus prepared is then mixed in a conventional manner with commonly available compositions such as oil-in-water emulsion, water-in-oil emulsion, hydrophilic ointment, petrolatum, balm base, spray formulation, etc. The concentration of the ester used in the compositions are the same as described above.

Gel compositions of the instant invention may be formulated by dissolving at least one ester in a vehicle prepared from ethanol, water, butylene glycol, and/or propylene glycol. A gelling agent such as xanthan gum, polyquaternium-10, methyl cellulose, ethyl cellulose, hydroxyethylcellulose, hydroxypropylcellulose, chitosan, hydroxypropylmethylcellulose, ammoniated glycyrrhizinate or carbomer is then added to the solution with agitation. The preferred concentration of the gelling agent may range from 0.1 to 2 percent by weight of the total composition. The concentration of the ester used in the compositions are the same as described above.

To prepare an actuated composition, a topical agent is incorporated into any one of the above formulations by dissolving or mixing the agent into the composition.

The duration of treatment necessary to effect detectible changes in the dermis will depend upon several factors, including the type and concentration of AHA ester employed, the frequency of application, the type of skin being treated, and the degree of natural aging, photoaging and/or photodamage present. Generally the time required to achieve detectible changes in the dermis, as measured by the technique described in the examples below, will be at least about one or two months, or perhaps at least three months, four months or more depending upon the factors mentioned above (especially the concentration of the ester and frequency of application). Treatment can be continued indefinitely. The AHA esters should be applied periodically, preferably once or twice per day, although applications of fewer times than daily are contemplated.

To achieve a visibly noticeable effect, for example a visible reduction in a facial wrinkle or in a skin line (sometimes also referred to as a fine line or fine wrinkle), may take about the same length of time or a little longer. Thus, within one month, two months, three months or more, one can achieve a visible reduction in skin lines and wrinkles and achieve a younger or more youthful appearance on facial skin and skin on other areas of the body. Such an effect can be referred to as an anti-aging effect.

Different combinations of the esters of this invention can be used in accordance with this invention. Such treatments also can be combined with treatments utilizing other anti-aging compounds such as alpha hydroxyacids, alpha ketoacids, alpha ketoacid esters and related compounds, and reaction products thereof, as disclosed in our U.S. Pat. No. 5,091,171. Those compounds provide the additional benefit of improving keratinization and thereby decreasing the incidence of dry skin. The portions of that patent listing the useful compounds for anti-aging are expressly incorporated herein by reference, especially the disclosure beginning at column 5, line 48, through column 11, line 53, and the recitations of such compounds at claims 9–20. Included within those compounds, for example, are glycolic acid, lactic acid, citric acid, isocitric acid, gluconic acid and gluconolactone, methyllactic acid, mandelic acid, galacturonic acid and galacturnolactone, quinic acid and quinolactone, tartaric acid, malic acid, ethyl pyruvate, tropic acid, ascorbic acid and isoascorbic acid and their lactones and isomers, benzylic acid, 2-phenyllactic acid, 3-phenyllactic acid, ribonic acid and ribonolactone, saccharic acid and saccharolactone, mucic acid and mucolactone, citramalic acid, galactonic acid and galactonolactone, gulonic acid and gulonolactone, glucuronic acid and glucuronolactone, pantoic acid and pantolactone, and glucoheptonic acid. Again, when alpha hydroxyacids, alpha ketoacids, and related compounds are employed, the concentration will range from at least about one or two percent to as much as five or ten percent or higher.

Such other anti-aging compounds, which may be considered "activators" as discussed above, may be applied simultaneously with the esters of this invention, or may be applied at different times. When simultaneous application is made, the ester and other compound can be in the same or different compositions.

EXAMPLES

The following are illustrative examples of formulations and compositions and clinical tests according to this invention. Although the examples utilize only selected compounds and formulations, it should be understood that the following examples are illustrative and not limited. Therefore, any of the aforementioned esters may be substituted according to the teachings of this invention in the following examples. In some instances, the alpha hydroxyacid esters were combined with an alpha hydroxyacid, alpha ketoacid or related compound as described in U.S. Pat. No. 5,091,171.

In order to measure and determine dermal effects produced by alpha hydroxyacid esters and related compounds on topical application the following methods were used.

Skin thickness was measured as follows. The skin was grasped with a 2×6 cm metal hinge, the internal faces of which were coated with emery cloth to prevent skin slippage, and was manually squeezed to threshold patient discomfort. Combined thickness of two whole-skin layers including thickness of the two hinge leaves was measured with engineering micrometer calipers. Thickness of the two hinge leaves was subtracted to determine actual 2 skin layer thickness.

Histologic studies were done as follows. Skin punch-biopsy 4 mm specimens were obtained from control and treated skin at the sites where skin thickness measurements had been made. These specimens were processed for light microscopy. Additionally, skin punch biopsy 3 mm specimens were taken from these sites for electron microscopy studies.

The specimens for light microscopy were placed in 10% buffered formalin, bisected, embedded in paraffin and cut to 5 micron sections. Sections were stained with hematoxylin and eosin; colloidal iron to evaluate dermal glycosaminoglycans; Verhoeff-van Gieson stain for elastic tissue; Masson's trichrome to evaluate collagen; and Fontana-Masson to evaluate melanin pigment.

For electron microscopy, tissue samples were fixed in 4% buffered glutaraldehyde. After washing in 0.1 Molar cacodylate buffer, specimens were post-fixed in 2% osmium tetroxide for 2 hours, and dehydrated in graded ethanol and then propylene oxide, followed by imbedding in Taab Epon 812. Ultra-thin sections were cut with a Porter-Blum MT2B ultramicrotome, stained with uranyl acetate and bismuth subnitrate, and examined via an Hitachi H-7000 electron microscope.

Epidermal thickness was measured by image analysis on paraffin-imbedded hematoxylin and eosin-stained sections. Histometric measurements of mean thickness of epidermis were performed using a Southern Micro Image Analysis System. Mean thickness of epidermis was expressed as area of epidermis/horizontal length. More than 2 mm of horizontal length was assessed in each individual. The thickness of the papillary dermis was measured using image analysis as described above.

Example 1

A cream composition containing 30% triethyl citrate was formulated as follows.

Triethyl citrate 30 g was dissolved in propylene glycol 5 ml. The solution thus prepared was mixed with hydrophilic ointment 65 g until a consistent cream was obtained. The cream had pH 2.6.

Example 2

A solution composition containing 10% glycolic acid ester was formulated as follows.

Methyl 2-hydroxyethanoate (methyl glycolate) 10 g was dissolved in ethanol 70 ml and propylene glycol 20 ml. The solution composition thus prepared contained 10% w/v methyl glycolate.

Example 3

A solution composition containing 25% glycolic acid ester was formulated as follows.

Ethyl 2-hydroxyethanoate (ethyl glycolate) 25 g was dissolved in ethanol 60 ml and butylene glycol 15 ml. The solution composition thus prepared contained 25% w/v ethyl glycolate.

Example 4

A solution composition containing 50% glycolic acid ester was formulated as follows.

Triethyl 2-hydroxypropane-1,2,3-trioate (triethyl citrate) 50 g was dissolved in ethanol 40 ml and propylene glycol 10 ml. The solution composition thus prepared contained 50% w/v triethyl citrate.

Example 5

A solution composition containing 80% glycolic acid ester was formulated as follows.

Ethyl L-2-hydroxypropanoate (ethyl lactate) 80 g was dissolved in ethanol 20 ml. The solution composition thus prepared contained 80% w/v ethyl lactate.

Example 6

A solution composition containing 95% glycolic acid ester was formulated as follows.

Methyl 2,2-dimethyl-2-hydroxyethanoate (methyl α-hydroxyisobutyrate) 95 g was dissolved in ethanol 5 ml. The solution composition thus prepared contained 95% w/v methyl α-hydroxyisobutyrate.

Example 7

A liquid composition containing 100% or full strength glycolic acid ester was prepared as follows.

Diethyl L-2,3-dihydroxybutane-1,4-dioate (diethyl tartrate) in liquid form at room temperature, full strength (greater than 98%), boiling point 278°–282°, density 1.21, 20 g was packaged in a one ounce plastic dispensing bottle. The composition thus packaged contained full strength diethyl tartrate.

Example 8

A solution composition containing 5% glycolic acid ester in oil-in-water emulsion was prepared as follows.

Ethyl DL-2-phenyl-2-hydroxyethanoate (ethyl mandelate) 5 g was dissolved in propylene glycol 10 ml. The solution was then mixed with hydrophilic ointment, USP grade 85 g and the mixing was continued until a uniform consistency was obtained. The cream composition thus prepared contained 5% w/v ethyl mandelate.

Example 9

A cream composition containing 10% glycolic acid ester in oil-in-water emulsion was prepared as follows.

Methyl DL-2-phenyl-2-hydroxyethanoate (methyl mandelate) 10 g was dissolved in propylene glycol 20 ml. The solution was then mixed with hydrophilic ointment, USP grade 70 g and the mixing was continued until a uniform consistency was obtained. The cream composition thus prepared contained 10% w/v methyl mandelate.

Example 10

A cream composition containing 30% glycolic acid ester in oil-in-water emulsion was prepared as follows.

Ethyl 2,2-dimethyl-2-hydroxyethanoate (ethyl α-hydroxyisobutyrate) 30 g was dissolved in propylene glycol 10 ml. The solution was then mixed with hydrophilic ointment, USP grade 60 g and the mixing was continued until a uniform consistency was obtained. The cream composition thus prepared contained 30% w/v ethyl α-hydroxyisobutyrate.

Example 11

A cream composition containing 40% glycolic acid ester in oil-in-water emulsion was prepared as follows.

Methyl L-2-methyl-3-hydroxypropanoate (methyl L-β-hydroxyisobutyrate) 40 g was dissolved in propylene glycol 10 ml. The solution was then mixed with hydrophilic ointment, USP grade 50 g and the mixing was continued until a uniform consistency was obtained. The cream composition thus prepared contained 40% w/v methyl L-β-hydroxyisobutyrate.

Example 12

An ointment composition containing a 10% glycolic acid ester in water-in-oil emulsion was prepared as follows.

Ethyl 2-hydroxyethanoate (ethyl glycolate) 10 g was dissolved in propylene glycol 10 ml. The solution was then mixed with a typical water-in-oil emulsion 80 g and the mixing was continued until a uniform consistency was obtained. The water non-washable ointment thus prepared contained 10% w/v ethyl glycolate.

Example 13

A gel composition containing 15% glycolic acid ester was formulated as follows.

Methyl 2-hydroxyethanoate (methyl glycolate) 15 g was dissolved in ethanol 40 ml, propylene glycol 15 ml and water 29 ml. Methylcellulose 1 g was added and the mixture was stirred until a uniform gel composition was obtained. The gel composition thus prepared contained 15% w/v methyl glycolate.

Example 14

A solution composition containing 50% glycolic acid ester was prepared as follows.

Diethyl L-2,3-dihydroxybutane-1,4-dioate (diethyl tartrate) 50 g was dissolved in ethanol 40 ml and propylene glycol 10 ml. The solution composition thus prepared contained 50% w/v diethyl tartrate.

Example 15

A cream composition containing 20% glycolic acid ester in oil-in-water emulsion was prepared as follows.

Methyl L-2-hydroxypropanoate (methyl L-lactate) 20 g was dissolved in propylene glycol 15 ml. The solution was then mixed with a typical oil-in-water emulsion 65 g and the mixing was continued until a uniform consistency was obtained. The cream composition thus prepared contained 20% w/v methyl L-lactate.

Example 16

A cream composition containing 30% glycolic acid ester in oil-in-water emulsion was prepared as follows.

Methyl 2-hydroxyethanoate (methyl glycolate) 30 g was dissolved in propylene glycol 15 ml. The solution was then mixed with a typical oil-in-water emulsion 55 g and the mixing was continued until a uniform consistency was obtained. The cream composition thus prepared contained 30% w/v methyl glycolate.

Example 17

A cream composition containing 40% glycolic acid ester in oil-in-water emulsion was prepared as follows.

Triethyl 2-hydroxypropane-1,2,3-trioate (triethyl citrate) 40 g was dissolved in propylene glycol 10 ml. The solution was then mixed with a typical oil-in-water emulsion 50 g and the mixing was continued until a uniform consistency was obtained. The cream composition thus prepared contained 40% w/v triethyl citrate.

Example 18

A solution composition containing 75% glycolic acid ester was prepared as follows.

Ethyl 2,2-dimethyl-2-hydroxyethanoate (ethyl α-hydroxyisobutyrate) 75 g was dissolved in ethanol 20 ml and propylene glycol 5 ml. The solution composition thus prepared contained 75% w/v ethyl α-hydroxyisobutyrate.

Example 19

A solution composition containing 70% glycolic acid ester was prepared as follows.

Methyl 3,4-O-isopropylidene-L-threonate 70 g was dissolved in ethanol 24 ml and propylene glycol 6 ml. The solution composition thus prepared contained 70% w/v methyl 3,4-O-isopropylidene-L-threonate.

Example 20

A cream composition containing 13.8% glycolic acid ester and 4.5% activator in oil-in-water emulsion was prepared as follows.

Triethyl 2-hydroxypropane-1,2,3-trioate (triethyl citrate) 13.8 g (0.05 mole) and DL-2-hydroxypropanoic acid (DL-lactic acid) 4.5 g (0.05 mole) were dissolved in propylene glycol 21.7 ml. The solution was then mixed with a typical oil-in-water emulsion 60 g and the mixing was continued until a uniform consistency was obtained. The cream composition thus prepared contained 13.8% w/v ethyl citrate and 4.5% DL-lactic acid as an activator.

Example 21

A cream composition containing 5.2% glycolic acid ester and 4.5% activator in oil-in-water emulsion was prepared as follows.

Methyl L-2-hydroxypropanoate (methyl L-lactate) 5.2 g (0.05 mole) and DL-2-hydroxypropanoic acid (DL-lactic acid) 4.5 g (0.05 mole) were dissolved in propylene glycol 20.3 ml. The solution was then mixed with a typical oil-in-water emulsion 70 g and the mixing was continued until a uniform consistency was obtained. The cream composition thus prepared contained 5.2% w/v methyl L-lactate and 4.5% DL-lactic acid as an activator.

Example 22

A cream composition containing 4.5% glycolic acid ester and 3.8% activator in oil-in-water emulsion was prepared as follows.

Methyl 2-hydroxyethanoate (methyl glycolate) 4.5 g (0.05 mole) and 2-hydroxyethanoic acid (glycolic acid) 3.8 g (0.05 mole) were dissolved in propylene glycol 21.7 ml. The solution was then mixed with a typical oil-in-water emulsion 70 g and the mixing was continued until a uniform consistency was obtained. The cream composition thus prepared contained 4.5% w/v methyl glycolate and 3.8% glycolic acid as an activator.

Example 23

A cream composition containing 6.6% glycolic acid ester and 8.9% activator in oil-in-water emulsion was prepared as follows.

Methyl 2,2-dimethyl-2-hydroxyethanoate (methyl α-hydroxyisobutyrate) 6.6 g (0.05 mole) and 2,3,4,5,6-pentahydroxyhexanoic acid lactone (gluconolactone) 8.9 g (0.05 mole) were dissolved in water 15 ml and propylene glycol 9.5 ml. The solution was then mixed with a typical oil-in-water emulsion 60 g and the mixing was continued until a uniform consistency was obtained. The cream composition thus prepared contained 6.6% w/v methyl α-hydroxyisobutyrate and 8.9% gluconolactone as an activator.

Example 24

A cream composition containing 13.8% glycolic acid ester and 5.8% activator in oil-in-water emulsion was prepared as follows.

Triethyl 2-hydroxypropane-1,2,3-trioate (triethyl citrate) 13.8 g (0.05 mole) and ethyl 2-ketopropanoate (ethyl pyruvate) 5.8 g (0.05 mole) were dissolved in propylene glycol 10.4 ml. The solution was then mixed with a typical oil-in-water emulsion 70 g and the mixing was continued until a uniform consistency was obtained. The cream composition thus prepared contained 13.8% w/v triethyl citrate and 5.8% ethyl pyruvate as an activator.

Example 25

A cream composition containing 10.3% glycolic acid ester and 5.8% activator in oil-in-water emulsion was prepared as follows.

Diethyl L-2,3-dihydroxybutane-1,4-dioate (diethyl tartrate) 10.3 g (0.05 mole) and ethyl 2-ketopropanoate (ethyl pyruvate) 5.8 g (0.05 mole) were dissolved in propylene glycol 13.9 ml. The solution was then mixed with a typical oil-in-water emulsion 70 g and the mixing was continued until a uniform consistency was obtained. The cream composition thus prepared contained 10.3% w/v diethyl tartrate and 5.8% ethyl pyruvate as an activator.

Example 26

A cream composition containing 9.0% glycolic acid ester and 7.6% activator in oil-in-water emulsion was prepared as follows. Ethyl DL-2-phenyl-2-hydroxyethanoate (ethyl mandelate) 9.0 g (0.05 mole) and DL-2-phenyl-2-hydroxyethanoic acid (mandelic acid) 7.6 g (0.05 mole) were dissolved in propylene glycol 23.6 ml. The solution was then mixed with a typical oil-in-water emulsion 60 g and the mixing was continued until a uniform consistency was obtained. The cream composition thus prepared contained 9.0% w/v ethyl mandelate and 7.6% mandelic acid as an activator.

Example 27

A cream composition containing 5.9% glycolic acid ester and 4.5% activator in oil-in-water emulsion was prepared as follows.

Methyl L-2-methyl-3-hydroxypropanoate (methyl L-β-hydroxyisobutyrate) 5.9 g (0.05 mole) and DL-2-hydroxypropanoic acid (DL-lactic acid) 4.5 g (0.05 mole) were dissolved in propylene glycol 19.6 ml. The solution was then mixed with a typical oil-in-water emulsion 70 g and the mixing was continued until a uniform consistency was obtained. The cream composition thus prepared contained 5.9% w/v methyl L-β-hydroxyisobutyrate and 4.5% DL-lactic acid as an activator.

Example 28

A female, age 78, treated her left forearm for two months with a placebo lotion topically applied twice daily. She applied 100% triethyl citrate topically twice daily to her right forearm. Skin thickness was measured as previously described. While the skin of the left forearm remained unchanged, the skin of the right forearm increased in thickness by 18%. This shows that triethyl citrate 100% on topical application increased skin thickness by 18%. The skin of the treated site also showed decreased numbers of age spots and other pigmented spots.

Example 29

A female, age 63, treated her right forearm for two months with a placebo lotion topically applied twice daily. She applied 100% triethyl citrate topically twice daily to her left forearm. Skin thickness was measured as previously described. While the skin of the right forearm remained unchanged, the skin of the left forearm increased in thickness by 7%. This shows that triethyl citrate 100% on topical application increased skin thickness by 7%.

Example 30

A female, age 53, treated her left forearm for two months with a placebo lotion topically applied twice daily. She applied 100% triethyl citrate topically twice daily to her right forearm. Skin thickness was measured as previously described. While the skin of the left forearm remained unchanged, the skin of the right forearm increased in thickness by 12%. This shows that triethyl citrate 100% on topical application increased skin thickness by 12%.

Example 31

A female, age 71, treated her right forearm for two months with a placebo lotion topically applied twice daily. She applied 100% triethyl citrate topically twice daily to her left forearm. Skin thickness was measured as previously described. While the skin of the right forearm remained unchanged, the skin of the left forearm increased in thickness by 30%. This shows that triethyl citrate 100% on topical application increased skin thickness by 30%. The skin of the treated site also showed decreased numbers of age spots and other pigmented spots.

Example 32

A female, age 73, treated her left forearm for one month with a placebo lotion topically applied twice daily. She applied 100% triethyl citrate topically twice daily to her right forearm. Skin thickness was measured as previously described. While the skin of the left forearm remained unchanged, the skin of the right forearm increased in thickness by 13%. This shows that triethyl citrate 100% on topical application increased skin thickness by 13%.

Example 33

A female, age 73, treated her left forearm for two months with a placebo lotion topically applied twice daily. She applied 100% diethyl tartrate topically twice daily to her right forearm. Skin thickness was measured as previously described. While the skin of the left forearm remained unchanged, the skin of the right forearm increased in thickness by 6%. This shows that diethyl tartrate 100% on topical application increased skin thickness by 6%.

Example 34

A male, age 73, treated his right forearm for one month with a placebo lotion topically applied twice daily. He applied 30% methyl mandelate lotion topically twice daily to the left forearm. Skin thickness was measured as previously described. While the skin of the right forearm remained unchanged, the skin of the left forearm increased in thickness by 12%. This shows that methyl mandelate 30% on topical application increased skin thickness by 12%.

TEST RESULTS

Some test results of the instant invention have been described in the prior sections including the aforementioned Examples. Descriptions and discussions presented in this section are considered as supplemental to and as summaries of the previous test results.

The compositions containing alpha hydroxyacid esters or related compounds with or without an activator were topically applied twice daily to one forearm and a placebo vehicle to the other forearm of volunteers or patients for various periods of time. Both during and at the end of the test periods, the skin thickness of treated sites including the skin treated with the placebo vehicle was measured according to the aforementioned method. At the end of the test periods, 4 mm punch biopsy specimens were obtained from both control and treated skin at the sites where skin thickness measurements had been made. These specimens were processed for light microscopy. Additionally, 3 mm punch biopsy skin specimens were taken from these sites for electron microscopy studies. All specimens were stained and processed as described previously herein.

In general, histometric measurement using image analysis showed increased thickness of the epidermis in the skin treated with alpha hydroxyacid esters or related compounds. Histologic measurement also showed increased thickness of the papillary dermis in the skin treated with alpha hydroxyacid esters or related compounds.

The results of whole skin thickness measured by micrometer calipers were shown as follows.

| Compound | Volunteer Age, Sex | Duration of Treatment (Days) | Skin Thickness Increase (%) |
|---|---|---|---|
| Triethyl Citrate | 78 F | 62 | 18 |
| | 63 F | 62 | 7 |
| | 53 F | 55 | 12 |
| | 71 F | 54 | 30 |
| | 73 F | 34 | 13 |
| Diethyl Tartrate | 73 F | 55 | 6 |
| Methyl Mandelate | 73 M | 30 | 12 |

Increase In Thickness of Forearm Skin After Topical Application of Alpha Hydroxyacid Esters or Related Compounds It is seen from the above table that compositions containing alpha hydroxyacid esters or related compounds of the instant invention on topical application have produced increased thickness of the treated skin, whereas there are no detectable changes in the thickness of skin treated with the placebo vehicle. Compositions containing alpha hydroxyacid esters or related compounds incorporated with an activator including ethyl pyruvate, etc., appear to provide faster results.

Histologic sections with magnification of 10×, from biopsy specimens of skin treated with alpha hydroxyacid esters or related compounds and stained with colloidal iron, showed increased production of glycosaminoglycans as compared to the control skin treated with the placebo vehicle.

Histologic sections with magnification of 20×, from biopsy specimens of skin treated with alpha hydroxyacid esters or related compounds and stained with hematoxylin and eosin or Gomori trichrome, showed increased production of collagen fibers as compared to the control skin treated with the placebo vehicle.

Histologic sections with magnification of 10×, from biopsy specimens of skin treated with alpha hydroxyacid esters or related compounds and stained with Verhoeff-van Gieson stain, showed more orderly arrangement and uniformity of elastin fibers as compared to the control skin treated with the placebo vehicle.

Based on electromicroscopic studies, the skin treated with compositions containing alpha hydroxyacid esters or related compounds showed more uniform distribution and less density and clumping of melanin granules in the basal cell layers at the dermal-epidermal junction.

Histochemical studies showed there were no detectable signs of inflammation in the epidermis or dermis of the skin treated with alpha hydroxyacid esters or related compounds, as in contrast to reported findings in skin treated with retinoic acid.

As mentioned previously, collagen fibers provide tensile strength of the skin, elastic fibers give resilience to the dermis, and glycosaminoglycans bind water to form a gelatinous mass between the collagen and elastic fibers which acts as a lubricant and shock absorber for the dermis. In aging skin, the collagen fibers decrease in numbers, the elastic fibers become fragmented and less organized, and the dermis is less hydrated by glycosaminoglycans. In photoaging skin, the melanin granules become clumped and increased in density, resulting in formation of age spots and other pigmented spots. Therefore, aging skin shows signs of age spots, skin lines, fine and coarse wrinkles, and skin changes associated with aging and photoaging.

In general, compositions containing alpha hydroxyacid esters or related compounds have higher pH than that of the parent alpha hydroxyacids. Such attribute is beneficial for the formulation of cosmetic as well as dermatologic compositions. In addition, compositions containing alpha hydroxyacid esters or related compounds appeared to be slow-release formulations in that the active ingredients (free alpha hydroxyacids) are released after percutaneous penetration into the skin.

Based on the above, alpha hydroxyacid esters and related compounds are beneficial for topical management as well as treatment of age spots, skin lines, fine and coarse wrinkles, and skin changes associated with aging and photoaging. They produce an anti-aging effect that leaves the skin looking younger or more youthful.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A method of treating aging related skin conditions comprising topically applying to the skin, for a period of time and in an amount sufficient to effect changes in the dermis, of an alpha hydroxyacid ester selected from the group consisting of compounds of the formula:

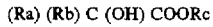

(Ra) (Rb) C (OH) COORc wherein Ra and Rb independently are selected from the group consisting of H, F, Cl, I, Br, alkyl, aralkyl or aryl group of saturated or unsaturated, isomeric or non-isomeric, straight or branched chain or cyclic form, having 1 to 29 carbon atoms, and in addition Ra and Rb may carry OH, CHO, COOH and alkoxy group having 1 to 9 carbon atoms, Rc is alkyl, aralkyl or aryl group of saturated or unsaturated, isomeric or non-isomeric, straight or branched chain or cyclic form, having 1 to 19 carbon atoms, and wherein the ester may exist as a stereoisomer in D, L, and DL forms when Ra and Rb are not identical, and wherein when the ester contains two or more carboxyl groups the ester can exist as partial or full ester form.

2. A method according to claim 1, wherein said alpha hydroxyacid ester is topically applied to reduce the presence of pigmented and non-pigmented age spots.

3. A method according to claim 1, wherein said alpha hydroxyacid ester is topically applied to effect a substantial increase in skin thickness.

4. A method according to claim 1, wherein said alpha hydroxyacid ester is topically applied to stimulate synthesis of a dermal component selected from the group consisting of glycosaminoglycans, proteoglycans, collagen and elastic fibers.

5. A method according to claim 1, wherein said alpha hydroxyacid ester is topically applied to effect a detectable decrease in skin lines.

6. A method according to claim 1, wherein said alpha hydroxyacid ester is topically applied to effect a detectable decrease in wrinkles.

7. A method according to claim 1, wherein said alpha hydroxyacid ester is topically applied to photoaged skin.

8. A method according to claim 1, wherein said alpha hydroxyacid ester is topically applied to photodamaged skin.

9. A method according to claim 1, wherein said alpha hydroxyacid ester is topically applied to intrinsically aged skin.

10. A method according to claim 1, wherein Ra and Rb are independently selected from the groups of C1–C5, C6–C10, C11–C15, C16–C20, C21–C25 and C26–C29, and wherein Rc is independently selected from the groups of C1–C5, C6–C10, C11–C15 and C16–C19.

11. A method according to claim 1, wherein Ra, Rb and Rc are independently selected from the group consisting of methyl, ethyl, propyl, isopropyl, butyl, pentyl, octyl, decyl, dodecyl, hexadecyl, benzyl, and phenyl.

12. A method according to claim 1, wherein said alpha hydroxyacid ester is an alkyl hydroxyacid ester selected from the group consisting of:

the methyl, ethyl, propyl, isopropyl, butyl, pentyl, octyl, decyl and dodecyl esters of glycolic acid;

the methyl, ethyl, propyl, isopropyl, butyl, pentyl, octyl, decyl and dodecyl esters of lactic acid;

the methyl, ethyl, propyl, isopropyl, butyl, pentyl, octyl, decyl and dodecyl esters of methyllactic acid;

the methyl, ethyl, propyl, isopropyl, butyl, pentyl, octyl, decyl and dodecyl esters of 2-hydroxybutanoic acid;

the methyl, ethyl, propyl, isopropyl, butyl, pentyl, octyl, decyl and dodecyl esters of 2-hydroxypentanoic acid;

the methyl, ethyl, propyl, isopropyl, butyl, pentyl, octyl, decyl and dodecyl esters of 2-hydroxyhexanoic acid;

the methyl, ethyl, propyl, isopropyl, butyl, pentyl, octyl, decyl and dodecyl esters of 2-hydroxyheptanoic acid;

the methyl, ethyl, propyl, isopropyl, butyl, pentyl, octyl, decyl and dodecyl esters of 2-hydroxyoctanoic acid;

the methyl, ethyl, propyl, isopropyl, butyl, pentyl, octyl, decyl and dodecyl esters of 2-hydroxynonanoic acid;

the methyl, ethyl, propyl, isopropyl, butyl, pentyl, octyl, decyl and dodecyl esters of 2-hydroxydecanoic acid;

the methyl, ethyl, propyl, isopropyl, butyl, pentyl, octyl, decyl and dodecyl esters of 2-hydroxyundecanoic acid;

the methyl, ethyl, propyl, isopropyl, butyl, pentyl, octyl, decyl and dodecyl esters of 2-hydroxydodecanoic acid;

the methyl, ethyl, propyl, isopropyl, butyl, pentyl, octyl, decyl and dodecyl esters of 2-hydroxytetradecanoic acid;

the methyl, ethyl, propyl, isopropyl, butyl, pentyl, octyl, decyl and dodecyl esters of 2-hydroxyhexadecanoic acid;

the methyl, ethyl, propyl, isopropyl, butyl, pentyl, octyl, decyl and dodecyl esters of 2-hydroxyoctadecanoic acid;

the methyl, ethyl, propyl, isopropyl, butyl, pentyl, octyl, decyl and dodecyl esters of 2-hydroxyeicosanoic acid;

the methyl, ethyl, propyl, isopropyl, butyl, pentyl, octyl, decyl and dodecyl esters of 2-hydroxytetraeicosanoic acid; and the methyl, ethyl, propyl, isopropyl, butyl, pentyl, octyl, decyl and dodecyl esters of 2-hydroxytetraeicosenoic acid.

13. A method according to claim 1, wherein said alpha hydroxyacid ester is an aralkyl or aryl 2-hydroxycarboxylic acid ester selected from the group consisting of:

the methyl, ethyl, propyl, isopropyl, butyl, pentyl, octyl, decyl and dodecyl esters of 2-phenyl 2-hydroxyethanoic acid esters;

the methyl, ethyl, propyl, isopropyl, butyl, pentyl, octyl, decyl and dodecyl esters of 2,2-diphenyl 2-hydroxyethanoic acid;

the methyl, ethyl, propyl, isopropyl, butyl, pentyl, octyl, decyl and dodecyl esters of 3-phenyl 2-hydroxypropanoic acid; and the methyl, ethyl, propyl, isopropyl, butyl, pentyl, octyl, decyl and dodecyl esters of 2-phenyl 2-methyl 2-hydroxyethanoic acid.

14. A method according to claim 1, wherein said alpha hydroxyacid ester is an polyhydroxyacid ester selected from the group consisting of:

the methyl, ethyl, propyl, isopropyl, butyl, pentyl, octyl, decyl, dodecyl, phenyl and benzyl esters of 2,3-dihydroxypropanoic acid;

the methyl, ethyl, propyl, isopropyl, butyl, pentyl, octyl, decyl, dodecyl, phenyl and benzyl esters of 2,3,4-trihydroxybutanoic acid and its isomers including erythronic acid and threonic acid;

the methyl, ethyl, propyl, isopropyl, butyl, pentyl, octyl, decyl, dodecyl, phenyl and benzyl esters of 2,3,4,5-tetrahydroxypentanoic acid and its isomers including ribonic acid, arabinoic acid, xylonic acid and lyxonic acid;

the methyl, ethyl, propyl, isopropyl, butyl, pentyl, octyl, decyl, dodecyl, phenyl and benzyl esters of 2,3,4,5,6-pentahydroxyhexanoic acid and its isomers including allonic acid, altronic acid, gluconic acid, mannoic acid, gulonic acid, idonic acid, galactonic acid, and talonic acid;

the methyl, ethyl, propyl, isopropyl, butyl, pentyl, octyl, decyl, dodecyl, phenyl and benzyl esters of 2,3,4,5,6,7-hexahydroxyheptanoic acid and its isomers including glucoheptonic acid and galactoheptonic acid;

the methyl, ethyl, propyl, isopropyl, butyl, pentyl, octyl, decyl, dodecyl, phenyl and benzyl esters of glyceruronic acid;

the methyl, ethyl, propyl, isopropyl, butyl, pentyl, octyl, decyl, dodecyl, phenyl and benzyl esters of erythruronic acid; etc., the methyl, ethyl, propyl, isopropyl, butyl, pentyl, octyl, decyl, dodecyl, phenyl and benzyl esters of threuronic acid;

the methyl, ethyl, propyl, isopropyl, butyl, pentyl, octyl, decyl, dodecyl, phenyl and benzyl esters of riburonic acid;

the methyl, ethyl, propyl, isopropyl, butyl, pentyl, octyl, decyl, dodecyl, phenyl and benzyl esters of arabinuronic acid;

the methyl, ethyl, propyl, isopropyl, butyl, pentyl, octyl, decyl, dodecyl, phenyl and benzyl esters of xyluronic acid;

the methyl, ethyl, propyl, isopropyl, butyl, pentyl, octyl, decyl, dodecyl, phenyl and benzyl esters of lyxuronic acid;

the methyl, ethyl, propyl, isopropyl, butyl, pentyl, octyl, decyl, dodecyl, phenyl and benzyl esters of alluronic acid;

the methyl, ethyl, propyl, isopropyl, butyl, pentyl, octyl, decyl, dodecyl, phenyl and benzyl esters of altruronic acid;

the methyl, ethyl, propyl, isopropyl, butyl, pentyl, octyl, decyl, dodecyl, phenyl and benzyl esters of glucuronic acid;

the methyl, ethyl, propyl, isopropyl, butyl, pentyl, octyl, decyl, dodecyl, phenyl and benzyl esters of mannuronic acid;

the methyl, ethyl, propyl, isopropyl, butyl, pentyl, octyl, decyl, dodecyl, phenyl and benzyl esters of guluronic acid;

the methyl, ethyl, propyl, isopropyl, butyl, pentyl, octyl, decyl, dodecyl, phenyl and benzyl esters of iduronic acid;

the methyl, ethyl, propyl, isopropyl, butyl, pentyl, octyl, decyl, dodecyl, phenyl and benzyl esters of galacturonic acid; and the methyl, ethyl, propyl, isopropyl, butyl, pentyl, octyl, decyl, dodecyl, phenyl and benzyl esters of taluronic acid.

15. A method according to claim 1, wherein said alpha hydroxyacid ester is a hydroxypolyacid ester selected from the group consisting of:

the methyl, ethyl, propyl, isopropyl, butyl, pentyl, octyl, decyl, dodecyl, phenyl and benzyl esters of 2-hydroxypropane-1,3-dioic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2-hydroxybutane-1,4-dioic acid esters;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2,3-dihydroxybutane-1,4-dioic acid; and the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of 3-hydroxy-3-carboxypentane-1,5-dioic acid.

16. A method according to claim 1, wherein said alpha hydroxyacid ester is a polyhydroxypolyacid ester.

17. A method according to claim 16, wherein said polyhydroxypolyacid ester is selected from the group consisting of the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2,3,4,5-tetrahydroxyhexane-1,6-dioic acid and its isomers including glucaric acid and galactaric acid.

18. A method according to claim 1, wherein the concentration of alpha hydroxyacid ester employed is at least five percent by weight.

19. A method according to claim 1, wherein the concentration of alpha hydroxyacid ester employed is at least ten percent by weight.

20. A method according to claim 1, further comprising the step of topically applying an alpha hydroxyacid selected from the group consisting of compounds of the formula:

(Ra) (Rb) C (OH) COOH wherein Ra and Rb independently are selected from the group consisting of H, F, Cl, I, Br, alkyl, aralkyl or aryl group of saturated or unsaturated, isomeric or non-isomeric, straight or branched chain or cyclic form, having 1 to 29 carbon atoms, and in addition Ra and Rb may carry OH, CHO, COOH and alkoxy group having 1 to 9 carbon atoms, wherein the acid may exist as a stereoisomer in D, L, and DL forms when Ra and Rb are not identical, and may exist in a lactone form when it contains two or more hydroxy groups, and wherein the alpha hydroxyacid may exist as a salt or reaction product with an amphoteric or pseudoamphoteric compound.

21. A method according to claim 20, wherein the said alpha hydroxyacid is present in the same composition as the alpha hydroxyacid ester.

22. A method according to claim 20, wherein said alpha hydroxyacid is present in a different composition than the composition comprising the alpha hydroxyacid ester.

23. A method according to claim 20, wherein the concentration of said alpha hydroxyacid is at least one percent by weight.

24. A method according to claim 20, wherein the concentration of said alpha hydroxyacid is at least three percent by weight.

25. A method according to claim 1, further comprising the step of topically applying a cosmetic or topically active agent.

26. A method according to claim 25, wherein said topically active agent is selected from the group consisting of acyclovir, amphotericins, chlorhexidine, clotrimazole, ketoconazole, econazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate).

27. A method of treating aging related skin conditions comprising topically applying to the skin, for a period of time and in an amount sufficient to effect changes in the dermis or epidermis, of a compound selected from the group consisting of:

the methyl, ethyl, propyl, isopropyl, butyl, pentyl, octyl, decyl, dodecyl, phenyl and benzyl esters of 3-hydroxybutanoic acid;

the methyl, ethyl, propyl, isopropyl, butyl, pentyl, octyl, decyl, dodecyl, phenyl and benzyl esters of ascorbic acid and isoascorbic acid;

the methyl, ethyl, propyl, isopropyl, butyl, pentyl, octyl, decyl, dodecyl, phenyl and benzyl esters of quinic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of isocitric acid;

the methyl, ethyl, propyl, isopropyl, butyl, pentyl, octyl, decyl, dodecyl, phenyl and benzyl esters of tropic acid;

the methyl, ethyl, propyl, isopropyl, butyl, pentyl, octyl, decyl, dodecyl, phenyl and benzyl esters of trethocanic acid;

the methyl, ethyl, propyl, isopropyl, butyl, pentyl, octyl, decyl, dodecyl, phenyl and benzyl esters of 3-chlorolactic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of citramalic acid;

the methyl, ethyl, propyl, isopropyl, butyl, pentyl, octyl, decyl, dodecyl, phenyl and benzyl esters of agaricic acid;

the methyl, ethyl, propyl, isopropyl, butyl, pentyl, octyl, decyl, dodecyl, phenyl and benzyl esters of aleuritic acid;

the methyl, ethyl, propyl, isopropyl, butyl, pentyl, octyl, decyl, dodecyl, phenyl and benzyl esters of pantoic acid;

the methyl, ethyl, propyl, isopropyl, butyl, pentyl, octyl, decyl, dodecyl, phenyl and benzyl esters of lactobionic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of piscidic acid; and the methyl, ethyl, propyl, isopropyl, butyl, pentyl, octyl, decyl and dodecyl esters of hexulosonic acid.

28. A composition suitable for topical application to the skin comprising at least five percent by weight of an alpha hydroxyacid ester selected from the group consisting of compounds of the formula:

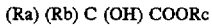

(Ra) (Rb) C (OH) COORc wherein Ra and Rb independently are selected from the group consisting of H, F, I, Cl, Br, alkyl, aralkyl or aryl group of saturated or unsaturated, isomeric or non-isomeric, straight or branched chain or cyclic form, having 1 to 29 carbon atoms, and in addition Ra and Rb may carry OH, CHO, COOH and alkoxy group having 1 to 9 carbon atoms. Rc is alkyl, aralkyl or aryl group of saturated or unsaturated, isomeric or non-isomeric, straight or branched chain or cyclic form, having 1 to 19 carbon atoms, and wherein the ester may exist as a stereoisomer in D, L, and DL forms when Ra and Rb are not identical, and wherein when the ester contains two or more carboxyl groups the ester can exist as partial or full ester form.

29. A composition according to claim 28, wherein Ra, Rb and Rc are independently selected from the group consisting of methyl, ethyl, propyl, isopropyl, butyl, pentyl, octyl, decyl, dodecyl, hexadecyl, benzyl, and phenyl.

30. A composition according to claim 28, wherein said alpha hydroxyacid ester is an alkyl hydroxyacid ester selected from the group consisting of:

the methyl, ethyl, propyl, isopropyl, butyl, pentyl, octyl, decyl and dodecyl esters of glycolic acid;

the methyl, ethyl, propyl, isopropyl, butyl, pentyl, octyl, decyl and dodecyl esters of lactic acid;

the methyl, ethyl, propyl, isopropyl, butyl, pentyl, octyl, decyl and dodecyl esters of methyllactic acid;

the methyl, ethyl, propyl, isopropyl, butyl, pentyl, octyl, decyl and dodecyl esters of 2-hydroxybutanoic acid;

the methyl, ethyl, propyl, isopropyl, butyl, pentyl, octyl, decyl and dodecyl esters of 2-hydroxypentanoic acid;

the methyl, ethyl, propyl, isopropyl, butyl, pentyl, octyl, decyl and dodecyl esters of 2-hydroxyhexanoic acid;

the methyl, ethyl, propyl, isopropyl, butyl, pentyl, octyl, decyl and dodecyl esters of 2-hydroxyheptanoic acid;

the methyl, ethyl, propyl, isopropyl, butyl, pentyl, octyl, decyl and dodecyl esters of 2-hydroxyoctanoic acid;

the methyl, ethyl, propyl, isopropyl, butyl, pentyl, octyl, decyl and dodecyl esters of 2-hydroxynonanoic acid;

the methyl, ethyl, propyl, isopropyl, butyl, pentyl, octyl, decyl and dodecyl esters of 2-hydroxydecanoic acid;

the methyl, ethyl, propyl, isopropyl, butyl, pentyl, octyl, decyl and dodecyl esters of 2-hydroxyundecanoic acid;

the methyl, ethyl, propyl, isopropyl, butyl, pentyl, octyl, decyl and dodecyl esters of 2-hydroxydodecanoic acid;

the methyl, ethyl, propyl, isopropyl, butyl, pentyl, octyl, decyl and dodecyl esters of 2-hydroxytetradecanoic acid;

the methyl, ethyl, propyl, isopropyl, butyl, pentyl, octyl, decyl and dodecyl esters of 2-hydroxyhexadecanoic acid;

the methyl, ethyl, propyl, isopropyl, butyl, pentyl, octyl, decyl and dodecyl esters of 2-hydroxyoctadecanoic acid;

the methyl, ethyl, propyl, isopropyl, butyl, pentyl, octyl, decyl and dodecyl esters of 2-hydroxyeicosanoic acid;

the methyl, ethyl, propyl, isopropyl, butyl, pentyl, octyl, decyl and dodecyl esters of 2-hydroxytetraeicosanoic acid; and the methyl, ethyl, propyl, isopropyl, butyl, pentyl, octyl, decyl and dodecyl esters of 2-hydroxytetraeicosenoic acid.

31. A composition according to claim 28, wherein said alpha hydroxyacid ester is an aralkyl or aryl 2-hydroxycarboxylic acid ester selected from the group consisting of:

the methyl, ethyl, propyl, isopropyl, butyl, pentyl, octyl, decyl and dodecyl esters of 2-phenyl 2-hydroxyethanoic acid esters;

the methyl, ethyl, propyl, isopropyl, butyl, pentyl, octyl, decyl and dodecyl esters of 2,2-diphenyl 2-hydroxyethanoic acid;

the methyl, ethyl, propyl, isopropyl, butyl, pentyl, octyl, decyl and dodecyl esters of 3-phenyl 2-hydroxypropanoic acid; and the methyl, ethyl, propyl, isopropyl, butyl, pentyl, octyl, decyl and dodecyl esters of 2-phenyl 2-methyl 2-hydroxyethanoic acid.

32. A composition according to claim 28, wherein said alpha hydroxyacid ester is an polyhydroxyacid ester selected from the group consisting of:

the methyl, ethyl, propyl, isopropyl, butyl, pentyl, octyl, decyl, dodecyl, phenyl and benzyl esters of 2,3-dihydroxypropanoic acid;

the methyl, ethyl, propyl, isopropyl, butyl, pentyl, octyl, decyl, dodecyl, phenyl and benzyl esters of 2,3,4-trihydroxybutanoic acid and its isomers including erythronic acid and threonic acid;

the methyl, ethyl, propyl, isopropyl, butyl, pentyl, octyl, decyl, dodecyl, phenyl and benzyl esters of 2,3,4,5-tetrahydroxypentanoic acid and its isomers including ribonic acid, arabinoic acid, xylonic acid and lyxonic acid;

the methyl, ethyl, propyl, isopropyl, butyl, pentyl, octyl, decyl, dodecyl, phenyl and benzyl esters of 2,3,4,5,6-pentahydroxyhexanoic acid and its isomers including allonic acid, altronic acid, gluconic acid, mannoic acid, gulonic acid, idonic acid, galactonic acid, and talonic acid;

the methyl, ethyl, propyl, isopropyl, butyl, pentyl, octyl, decyl, dodecyl, phenyl and benzyl esters of 2,3,4,5,6,7-hexahydroxyheptanoic acid and its isomers including glucoheptonic acid and galactoheptonic acid;

the methyl, ethyl, propyl, isopropyl, butyl, pentyl, octyl, decyl, dodecyl, phenyl and benzyl esters of glyceruronic acid;

the methyl, ethyl, propyl, isopropyl, butyl, pentyl, octyl, decyl, dodecyl, phenyl and benzyl esters of erythruronic acid; etc.

the methyl, ethyl, propyl, isopropyl, butyl, pentyl, octyl, decyl, dodecyl, phenyl and benzyl esters of threuronic acid;

the methyl, ethyl, propyl, isopropyl, butyl, pentyl, octyl, decyl, dodecyl, phenyl and benzyl esters of riburonic acid;

the methyl, ethyl, propyl, isopropyl, butyl, pentyl, octyl, decyl, dodecyl, phenyl and benzyl esters of arabinuronic acid;

the methyl, ethyl, propyl, isopropyl, butyl, pentyl, octyl, decyl, dodecyl, phenyl and benzyl esters of xyluronic acid;

the methyl, ethyl, propyl, isopropyl, butyl, pentyl, octyl, decyl, dodecyl, phenyl and benzyl esters of lyxuronic acid;

the methyl, ethyl, propyl, isopropyl, butyl, pentyl, octyl, decyl, dodecyl, phenyl and benzyl esters of alluronic acid;

the methyl, ethyl, propyl, isopropyl, butyl, pentyl, octyl, decyl, dodecyl, phenyl and benzyl esters of altruronic acid;

the methyl, ethyl, propyl, isopropyl, butyl, pentyl, octyl, decyl, dodecyl, phenyl and benzyl esters of glucuronic acid;

the methyl, ethyl, propyl, isopropyl, butyl, pentyl, octyl, decyl, dodecyl, phenyl and benzyl esters of mannuronic acid;

the methyl, ethyl, propyl, isopropyl, butyl, pentyl, octyl, decyl, dodecyl, phenyl and benzyl esters of guluronic acid;

the methyl, ethyl, propyl, isopropyl, butyl, pentyl, octyl, decyl, dodecyl, phenyl and benzyl esters of iduronic acid;

the methyl, ethyl, propyl, isopropyl, butyl, pentyl, octyl, decyl, dodecyl, phenyl and benzyl esters of galacturonic acid; and the methyl, ethyl, propyl, isopropyl, butyl, pentyl, octyl, decyl, dodecyl, phenyl and benzyl esters of taluronic acid.

33. A composition according to claim 28, wherein said alpha hydroxyacid ester is a hydroxypolyacid ester selected from the group consisting of:

the methyl, ethyl, propyl, isopropyl, butyl, pentyl, octyl, decyl, dodecyl, phenyl and benzyl esters of 2-hydroxypropane-1,3-dioic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2-hydroxybutane-1,4-dioic acid esters;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2,3-dihydroxybutane-1,4-dioic acid; and the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of 3-hydroxy-3-carboxypentane-1,5-dioic acid.

34. A composition according to claim 27, wherein said alpha hydroxyacid ester is a polyhydroxypolyacid ester.

35. A composition according to claim 33, wherein said polyhydroxypolyacid ester is selected from the group consisting of the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of 2,3,4,5-tetrahydroxyhexane-1,6-dioic acid and its isomers including glucaric acid and galactaric acid.

36. A composition according to claim 28, further comprising an alpha hydroxyacid selected from the group consisting of compounds of the formula:

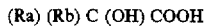

(Ra) (Rb) C (OH) COOH wherein Ra and Rb independently are selected from the group consisting of H, F, Cl, I, Br, alkyl, aralkyl or aryl group of saturated or unsaturated, isomeric or non-isomeric, straight or branched chain or cyclic form, having 1 to 29 carbon atoms, and in addition Ra and Rb may carry OH, CHO, COOH and alkoxy group having 1 to 9 carbon atoms, wherein the acid may exist as a stereoisomer in D, L, and DL forms when Ra and Rb are not identical, and may exist in a lactone form when the it contains two or more hydroxy groups, and wherein the alpha hydroxyacid may exist as a salt or reaction product with an amphoteric or pseudoamphoteric compound.

37. A composition according to claim 35, wherein the concentration of said alpha hydroxyacid is at least one percent by weight.

38. A composition according to claim 28, further comprising a cosmetic or topically active agent.

39. A composition according to claim 38, wherein said topically active agent is selected from the group consisting of acyclovir, amphotericins, chlorhexidine, clotrimazole, ketoconazole, exonazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate).

40. A composition suitable for topical application to the skin comprising at least five percent by weight of a compound selected from the group consisting of:

the methyl, ethyl, propyl, isopropyl, butyl, pentyl, octyl, decyl, dodecyl, phenyl and benzyl esters of 3-hydroxybutanoic acid;

the methyl, ethyl, propyl, isopropyl, butyl, pentyl, octyl, decyl, dodecyl, phenyl and benzyl esters of ascorbic acid and isoascorbic acid;

the methyl, ethyl, propyl, isopropyl, butyl, pentyl, octyl, decyl, dodecyl, phenyl and benzyl esters of quinic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of isocitric acid;

the methyl, ethyl, propyl, isopropyl, butyl, pentyl, octyl, decyl, dodecyl, phenyl and benzyl esters of tropic acid;

the methyl, ethyl, propyl, isopropyl, butyl, pentyl, octyl, decyl, dodecyl, phenyl and benzyl esters of trethocanic acid;

the methyl, ethyl, propyl, isopropyl, butyl, pentyl, octyl, decyl, dodecyl, phenyl and benzyl esters of 3-chlorolactic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl, dibenzyl, trimethyl, triethyl, tripropyl, triisopropyl, tributyl, tripentyl, trioctyl, tridecyl, tridodecyl, triphenyl and tribenzyl esters of citramalic acid;

the methyl, ethyl, propyl, isopropyl, butyl, pentyl, octyl, decyl, dodecyl, phenyl and benzyl esters of agaricic acid;

the methyl, ethyl, propyl, isopropyl, butyl, pentyl, octyl, decyl, dodecyl, phenyl and benzyl esters of aleuritic acid;

the methyl, ethyl, propyl, isopropyl, butyl, pentyl, octyl, decyl, dodecyl, phenyl and benzyl esters of pantoic acid;

the methyl, ethyl, propyl, isopropyl, butyl, pentyl, octyl, decyl, dodecyl, phenyl and benzyl esters of lactobionic acid;

the methyl, ethyl, propyl, isopropyl, butyl, pentyl, octyl, decyl, dodecyl, phenyl, benzyl, dimethyl, diethyl, dipropyl, diisopropyl, dibutyl, dipentyl, dioctyl, didecyl, didodecyl, diphenyl and dibenzyl esters of piscidic acid; and the methyl, ethyl, propyl, isopropyl, butyl, pentyl, octyl, decyl and dodecyl esters of hexulosonic acid.

41. A composition according to claim 40, wherein the concentration of said compound is at least ten percent by weight.

42. A composition according to claim 40, wherein the concentration of said compound is at least twenty percent by weight.

* * * * *